United States Patent [19]

Zhang et al.

[11] Patent Number: 5,229,519
[45] Date of Patent: Jul. 20, 1993

[54] PROCESS FOR PREPARING 2-HALO-5-HALOMETHYLPYRIDINES

[75] Inventors: Tony Y. Zhang, Indianapolis; Eric F. V. Scriven, Greenwood, both of Ind.

[73] Assignee: Reilly Industries, Inc., Indianapolis, Ind.

[21] Appl. No.: 846,898

[22] Filed: Mar. 6, 1992

[51] Int. Cl.$^5$ .......................................... C07D 213/61
[52] U.S. Cl. .................................................... 546/250
[58] Field of Search ........................................ 546/250

[56] References Cited

U.S. PATENT DOCUMENTS

| | | | |
|---|---|---|---|
| 4,245,098 | 1/1981 | Steiner et al. | 546/250 |
| 4,435,573 | 3/1984 | Lysenko et al. | 546/250 |
| 4,658,031 | 4/1987 | Hartmann et al. | 546/250 |
| 4,665,186 | 5/1987 | Steiner et al. | 546/250 |
| 4,871,859 | 10/1989 | Gupton et al. | |
| 4,987,232 | 1/1991 | Schroder. | |
| 5,026,854 | 6/1991 | Shepherd. | |
| 5,053,516 | 10/1991 | Hartmann et al. | |
| 5,106,984 | 4/1992 | Halpern et al. | 546/250 |
| 5,107,057 | 4/1992 | Chiang et al. | |

OTHER PUBLICATIONS

March, Jerry, "Advanced Organic Chemistry", 2 ed., McGraw-Hill, Inc., New York (1977), pp. 739–741.
Bryson et al., "Biological Probes. II. Ring Labeled Nicotinamide", *J. Org. Chem.*, vol. 39, No. 23, pp. 3436–3438 (1974).

*Primary Examiner*—Marianne M. Cintins
*Assistant Examiner*—John Peabody
*Attorney, Agent, or Firm*—Woodard, Emhardt, Naughton, Moriarty & McNett

[57] ABSTRACT

Disclosed are preferred processes for preparing a 2-halo-5-halomethylpyridine compound. The preferred processes involve cyclocondensing a 2-halo-2-halomethyl aldehyde or ketone of the formula (II)

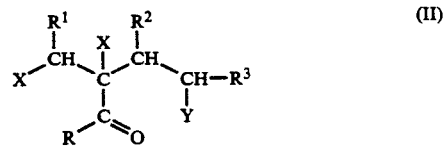

to form a 2-halo-2-halomethylpyridine compound of the formula (III)

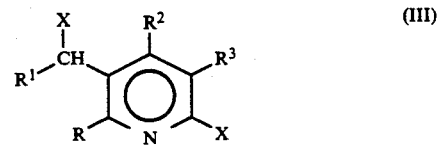

wherein X is Cl or Br, Y is a cyano group or an aminocarbonyl group, and R, $R^1$, $R^2$ and $R^3$ are, independently, H or an organic radical which does not interfere with the cyclocondensation.

9 Claims, No Drawings

PROCESS FOR PREPARING 2-HALO-5-HALOMETHYLPYRIDINES

BACKGROUND

This invention relates generally to a novel process for the preparation of 2-halo-5-halomethylpyridines. In a more particular sense, a preferred embodiment of this invention relates to such a process which includes cyclocondensing certain 2-halo-2-halomethyl aldehydes or ketones to form corresponding 2-halo-5-halomethylpyridines.

The importance of 2-chloro-5-chloromethylpyridines as pharmaceutical and agricultural intermediates has been well established. For example, 2-chloro-5-chloromethylpyridine can be used for synthesis of herbicide as described by European Patent 163855 (December 1985). Traditionally, 2-chloro-5-chloromethylpyridines have been prepared by chlorination of 2-chloro-5-methylpyridines or 2-chloro-5-hydroxymethylpyridines. For instance, conversion of 2-chloro-5-methylpyridine to 2-chloro-5-chloromethylpyridine was described in U.S. Pat. No. 4,778,896 to Gallenkamp. The preparation of the 2-chloro-5-methylpyridine starting material in this reaction has itself been the subject of several studies. U.S. Pat. No. 4,897,488 to Gallenkamp et al., European Patent Application 0324174 (December 1988), and German Patent Document DE 3839332 (May, 1990) relate to methods of converting 3-methylpyridine through its N-oxide derivative to 2-chloro-5-methylpyridine, along with isomeric 2-chloro-3-chloromethylpyridine which is difficult to separate. European Patent 108483 describes preparation of 2-chloro-5-methylpyridine from acyclic intermediate by ring synthesis, which includes a sequence of enamine formation, cycloaddition, ring opening, cyclization, oxidative aromatization and finally chlorination.

Conversion of 2-chloro-5-hydroxymethylpyridine to 2-chloro-5-chloromethylpyridine is described in *J. Heterocyclic Chem.*, 1979, 15, page 333, and U.S. Pat. No. 4,576,629 to Morland et al. The required intermediate 2-chloro-5-hydroxymethylpyridine was prepared from 6-chloro-3-pyridinecarboxylic acid by a sequence of transformations.

U.S. Pat. Nos. 4,990,622 and 4,958,025 both to Jelich describe a synthesis of 2-chloro-5-chloromethylpyridine from nicotinic acid through a five-step process. European Patent Application 0393453 (April 1990) describes a similar process, except starting from 3-dichloromethylpyridine.

All of these known processes of preparing 2-chloro-5-chloromethylpyridine have the disadvantages of low selectivity, prolonged and extensive reaction sequences, or harsh reaction conditions. Some also require the modification of substituent(s) on an existing pyridine ring.

Accordingly, there exists a continuing need and demand for processes for producing 2-halo-5-halomethylpyridines which are simple yet selective, and which can be conducted employing reaction conditions conducive to production on a reasonable scale with reasonable safety and process requirements. The applicants' invention addresses these needs.

SUMMARY OF THE INVENTION

One preferred embodiment of the present invention provides a process for preparing a 2-halo-5-halomethylpyridine compound, comprising a cyclocondensation reaction of a 2-halo-2-halomethyl aldehyde or ketone of the formula (III)

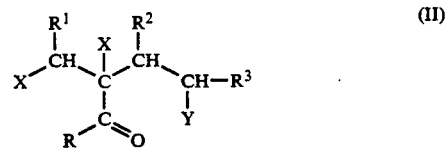

to form a 2-halo-2-halomethylpyridine compound of the formula (III)

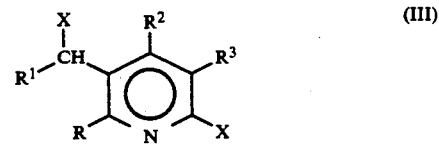

wherein in the above formulas X is Cl or Br, Y is a cyano group or an aminocarbonyl group, and R, $R^1$, $R^2$ and $R^3$ are, independently, H or an organic radical such as an aliphatic or aryl group, e.g. an optionally-substituted alkyl, alkenyl, alkynyl, or aryl (including heteroaryl) group. A preferred aspect of this embodiment is the preparation of the above-noted 2-halo-2-halomethyl aldehyde or ketone by halogenation of an α,β-unsaturated nitrile or amide (see e.g. formula I below).

Another preferred embodiment of the invention provides novel 2-halo-2-halomethyl aldehydes or ketones of the formula (II).

These embodiments provide highly attractive, simple and efficient routes to 2-halo-5-halomethylpyridine derivatives and precursors thereto and to other substituted pyridines. Further, starting materials are readily available and relatively inexpensive. Additional advantages and features of the invention will be apparent from the following description.

DESCRIPTION OF THE PREFERRED EMBODIMENTS

For the purposes of promoting an understanding of the principles of the invention, reference will now be made to certain embodiments and specific language will be used to describe the same. It will nevertheless be understood that no limitation of the scope of the invention is thereby intended, such alterations, further modifications and applications of the principles of the invention as described herein being contemplated as would normally occur to one skilled in the art to which the invention relates.

A preferred overall synthesis involves the halogenation of an α,β-unsaturated aldehyde or ketone of the formula (I)

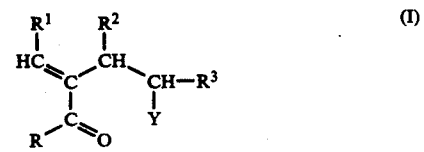

where Y is a cyano group (i.e. —CN) or an aminocarbonyl group (i.e. —CONH$_2$), and R, $R^1$, $R^2$ and $R^3$ are, independently, H or an organic radical, typically having up to about 20 carbon atoms, which does not interfere with the cyclocondensation reaction. For example, organic radicals satisfying R, R$^1$, R$^2$ and R$^3$ can be optionally-substituted alkyl, alkenyl, alkynyl, or aryl (including heteroaryl) groups. More typically, the organic radical is an aliphatic group, especially a lower aliphatic group (i.e. having 1 to 5 carbon atoms) such as lower alkyl. The stereochemistry of the C=C double bond shown in the compound of formula I can be cis or trans. Furthermore, compounds of formula I can be prepared from readily available starting materials. For example, they can be prepared by processes including the reaction of adducts (e.g. anthracene or cyclopentadiene adducts) of α,β-unsaturated aldehydes or ketones of the formula RCO—CH=CHR$^1$ with α,β-unsaturated nitriles or amides of the formula Y—C(R$^3$)=CHR$^2$ (e.g. acrylonitrile or acrylamide and substituted derivatives thereof), and the thermal decomposition of the resulting products to yield α,β-unsaturated nitriles or amides of the formula (I), as generally taught by F. Weiss et al., Belgian Patent No. 640,875 (Apr. 1, 1964) (abstracted at *Chem. Abstr.* 62:16062), and *Bull. Soc. Chim. France,* 1964, 550 (abstracted at *Chem. Abstr.* 61:2960), each of which is hereby incorporated herein by reference.

The halogenation is conducted with a suitable halogenating agent, for example elemental chlorine or bromine (i.e. Cl$_2$ or Br$_2$). The halogenation can be conducted with or without solvent, generally at a temperature range of about −20° C. to 100° C. Preferably, the halogenation is conducted at ambient temperature. When used, the solvent may be any one of the numerous solvents known to be suitable for halogenation of unsaturated compounds, for example, chlorinated hydrocarbons such as dichloromethane, 1,2-dichloroethane, carbon tetrachloride, etc., alcohols such as methanol, etc. The selection and use of suitable agents and solvents for the halogenation are well within the abilities of those skilled in the area.

The product of the halogenation step will be a 2-halo-5-halomethyl aldehyde or ketone of the formula (II)

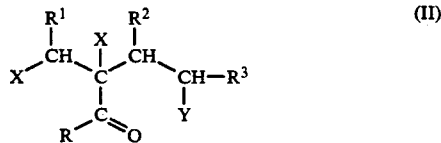

(II)

wherein R, R$^1$, R$^2$, R$^3$ and Y have the values given above and X is Cl or Br.

A second step of a preferred overall synthetic route involves a cyclocondensation reaction of compound of the formula (II) above so as to form a 2-halo-5-halomethylpyridine compound of the formula (III)

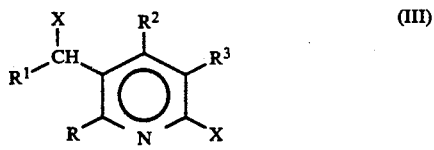

(III)

wherein X, R, R$^1$, R$^2$, R$^3$ and Y have the same values given above.

This cyclocondensation step is preferably conducted at a temperature of about 30° C. to 300° C., more preferably in the range of about 100° C., either in neat form or in the presence of a solvent. Preferred solvents include aromatic and aliphatic hydrocarbons, ethers, chlorinated hydrocarbons, carboxylic acids of less than four carbons, carboxylic esters, aliphatic nitriles, alkylamides such as N,N-dimethylformamide, etc., and the like. The reaction is best carried out in the absence of water, and thus a reagent or other material capable of removing water, e.g. PCl$_5$, PCl$_3$, POCl$_3$, P$_2$O$_5$, Ac$_2$O, CH$_3$COCl, MgSO$_4$, molecular sieve, etc. is preferably employed. Further, an anhydrous acid in the form of HX where X is halogen (e.g. Cl or Br) is preferably used as a promoter, and the reaction can be catalyzed by suitable known catalysts such as clay, Lewis acids, main group or transitional metal salts and complexes, etc. Also, in preferred cases, the cyclocondensation reaction is conducted under super atmospheric pressures.

Both the halogenation and the cyclocondensation steps can be carried out in any suitable fashion, ranging from batchwise to continuous, and the products recovered by conventional means such as extraction, distillation, etc. Further, the halogenation and cyclization steps can be combined in a single step procedure, i.e. halogenating the compound of formula I to obtain the compound of formula II and cyclizing the compound of formula II in situ (without isolation) to afford the compound of formula III.

In the above formulas, where R, R$^1$, R$^2$ and R$^3$ are designated as being optionally substituted, the substituent group or groups may be any of those customarily used in the development or synthesis of medicinal or pesticidal compounds. Representative substituents include groups such as alkyl, alkenyl, alkynyl (these usually having up to about 5 carbon atoms), aryl (e.g. phenyl, naphthyl.), cycloalkyl, hydroxyl, amino, halo (e.g. —Cl and —Br), etc.

For the purposes of promoting a further understanding of the invention and preferred features and advantages thereof, the following specific examples are provided. It will nevertheless be understood that these examples are illustrative and not limiting of the invention. In the following examples, certain abbreviations may appear. These will be taken to have their usual meaning. For instance, "h" means hours, "mL" means milliliters, "g" means grams, "mol" means moles, "mmol" means millimoles, etc.

EXAMPLE 1

2-Chloro-5-chloromethylpyridine

To a three necked, 100-mL round bottom equipped with a reflux condenser, gas inlet tube and a thermometer was charged 50 mL of N,N-dimethylformamide. Phosphorous pentachloride (2.3 g, 11 mmol) was added in several portions and anhydrous hydrogen chloride was introduced slowly. The reaction temperature was kept around 60° C.-85° C. by means of a water bath. 2-Chloro-2-chloromethyl-4-cyanobutyraldehyde in 5 mL of DMF was added at 80° C., through a syringe pump within a period of 1 h. The resulting mixture was then heated to 100° C. under stirring for 8 h, quenched with water, neutralized using NaHCO$_3$ to a pH of 5, extracted with methylene chloride, dried over MgSO$_4$, and concentrated and distilled to give 0.5 g of 2-chloro-5-chloromethylpyridine. Purity by GLC analysis was 95%.

EXAMPLE 2

2-Chloro-2-chloromethyl-4-cyanobutyraldehyde

A 50 ml round bottom flask was charged with a solution of 2-methylene-4-cyanobutyraldehyde in 5 mL of methylene chloride. The flask was immersed in a water bath and chlorine gas was bubbled into the solution. The solution was stirred for 10 minutes, excess chlorine and solvent were removed under reduced pressure to give the title compound in quantitative yield.

EXAMPLE 3

2-Methylene-4-cyanobutyraldehyde

A mixture of 2-cyanoethyl-5-norbornene-2-carboxaldehyde and 50 mL of dioctyl phthalate was degassed and heated at 230° C. under nitrogen pressure of 150 mm Hg for 3 h. The title compound was distilled out as a colorless liquid.

EXAMPLE 4

2-Cyanoethyl-5-norbornene-2-carboxaldehyde

To a solution of acrylonitrile in 50 mL of toluene was added at room temperature 2 mL of 10% aqueous solution of KOH. To this was added 5-norbornene-2-carboxaldehyde (6.1 g, 50 mmol) at ambient temperature within a period of 2 h. The resulting mixture was stirred for 6 h, quenched with 3 N aqueous HCl, extracted with toluene, dried over $MgSO_4$. Solvent and residual starting materials were removed to give the title compound.

EXAMPLE 5

2-Chloro-5-chloromethylpyridine

In a manner similar to that described in Example 1, the title compound is prepared by adding 4-chloro-4-chloromethyl-5-oxopentamide to a mixture of 3 grams of $PCL_5$ and 35 mL of N,N-dimethylformamide saturated with anhydrous HCl. The reaction is quenched with water, extracted and distilled to afford 2-chloro-5-chloromethylpyridine.

EXAMPLE 6

2-Chloro-3-methyl-5-chloromethylpyridine 4 grams of 2-chloro-2-chloromethyl-4-cyano-4-methylbutyraldehyde dissolved in 30 mL of acetonitrile is pumped concomitantly with anhydrous HCl into a pre-heated (180°–230° C.) flow reactor packed with $NiCl_2$-impregnated clay. Short path distillation gives 2-chloro-3-methyl-5-chloromethylpyridine as a liquid.

EXAMPLE 7

2-Chloro-3-(2,4-dichlorophenyl)-5-chloromethyl-6-methylpyridine

In a manner similar to that described in Example 1, the title compound is prepared from 2-chloro-2-chloromethyl-5-cyano-5-(2,4-dichlorophenyl)-pentane-2-one, N,N-dimethylformamide, $PCl_3$ an HCl. Workup and recrystallization yield the product as a white solid.

While the invention has been illustrated in detail in the foregoing description, the same is to be considered as illustrative and not restrictive in character, it being understood that only the preferred embodiment has been shown and described and that all changes and modifications that come within the spirit of the invention are desired to be protected.

What is claimed is:

1. A process for preparing a 2-halo-5-substituted pyridine compound, comprising:
halogenating an α,β-unsaturated aldehyde or ketone of the formula (I):

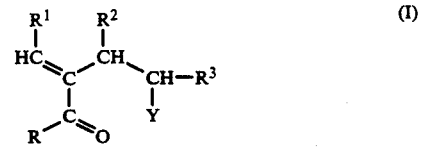

wherein Y is a cyano or aminocarbonyl group, and R, $R^1$, $R^2$ and $R^3$ are independently, H or an alkyl, alkenyl, alkynyl or aryl group having up to about 20 carbon atoms, to form a compound of the formula (II)

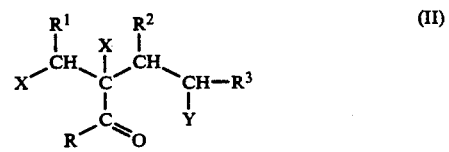

wherein Y, R, $R^1$, $R^2$ and $R^3$ have the same values as given above and X is Cl or Br, and, cyclocondensing the aldehyde or ketone of formula (II) to form a 2-halo-5-substituted pyridine compound of the formula (III)

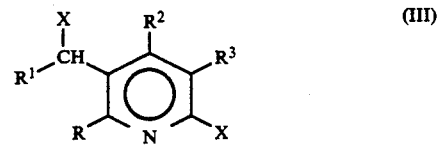

wherein Y, X, R, $R^1$, $R^2$ and $R^3$ have the same values as given above.

2. The process of claim 1 wherein Y is a cyano group.

3. The process of claim 1 wherein Y is an aminocarbonyl group.

4. The process of claim 1 wherein X is Cl and R, $R^1$, $R^2$ and $R^3$ are, independently, —H or a lower alkyl group.

5. The process of claim 4 wherein Y is a cyano group, R, $R^1$, $R^2$, $R^3$ are each H, and the formed 2-halo-5-halomethylpyridine is 2-chloro-5-chloromethylpyridine.

6. The process of claim 4 wherein Y is an aminocarbonyl group, R, $R^1$, $R^2$, $R^3$ are each H, and the formed 2-halo-5-halomethylpyridine is 2-chloro-5-chloromethylpyridine.

7. The process of claim 5, including the step of isolating the 2-chloro-5-chloromethylpyridine.

8. The process of claim 6, including the step of isolating the 2-chloro-5-chloromethylpyridine.

9. The process of claim 1 wherein R, $R^1$, $R^2$ and $R^3$ are, independently, —H, an alkyl group or an aryl group.

* * * * *